United States Patent
Liu et al.

(10) Patent No.: US 11,766,231 B2
(45) Date of Patent: Sep. 26, 2023

(54) SYSTEM AND METHOD OF IMAGE IMPROVEMENT FOR MULTIPLE PULSED X-RAY SOURCE-IN-MOTION TOMOSYNTHESIS APPARATUS USING ELECTROCARDIOGRAM SYNCHRONIZATION

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AIXSCAN INC., Sunnyvale, CA (US)

(*) Notice: Subject to any disclaimer, the term of this patent is extended or adjusted under 35 U.S.C. 154(b) by 204 days.

(21) Appl. No.: 17/523,373

(22) Filed: Nov. 10, 2021

(65) Prior Publication Data
US 2022/0313198 A1 Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2006.01)
*A61B 6/02* (2006.01)
(Continued)

(52) U.S. Cl.
CPC .............. *A61B 6/541* (2013.01); *A61B 6/025* (2013.01); *A61B 6/032* (2013.01); *A61B 6/035* (2013.01);
(Continued)

(58) Field of Classification Search
CPC ................................ A61B 6/025; A61B 6/541
See application file for complete search history.

(56) References Cited

U.S. PATENT DOCUMENTS

| | | |
|---|---|---|
| 2004/0077941 A1 | 4/2004 | Reddy et al. |
| 2004/0131140 A1* | 7/2004 | Bruder .................. A61B 6/503 378/4 |
| 2020/0202620 A1* | 6/2020 | Kiely .................... A61B 6/032 |

* cited by examiner

*Primary Examiner* — Dani Fox
(74) *Attorney, Agent, or Firm* — Patent PC; Bao Tran

(57) ABSTRACT

A system and method for improved image acquisition of multiple pulsed X-ray source-in-motion tomosynthesis imaging apparatus by generating the electrocardiogram (ECG) waveform data using an ECG device. Once a representative cardiac cycle is determined, system will acquire images only at rest period of heart beat. Real time ECG waveform is used as ECG synchronization for image improvement. The imaging apparatus avoids ECG peak pulse for better chest, lung and breast imaging under influence of cardiac periodical motion. As a result, smoother data acquisition, much higher data quality can be achieved. The multiple pulsed X-ray source-in-motion tomosynthesis machine is with distributed multiple X-ray sources that is spanned at wide scan angle. At rest period of one heartbeat, multiple X-ray exposures are acquired from X-ray sources at different angles. The machine itself has capability to acquire as many as 60 actual projection images within about two seconds.

20 Claims, 3 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.
| | | |
|---|---|---|
| *G06T 17/00* | (2006.01) | |
| *G01N 23/044* | (2018.01) | |
| *A61B 6/03* | (2006.01) | |
| *A61B 6/06* | (2006.01) | |
| *G01N 23/083* | (2018.01) | |
| *G01N 23/18* | (2018.01) | |
| *G06T 7/00* | (2017.01) | |
| *G06T 11/00* | (2006.01) | |
| *A61B 6/04* | (2006.01) | |
| *G06T 7/11* | (2017.01) | |
| *G16H 10/60* | (2018.01) | |
| *G16H 30/20* | (2018.01) | |
| *G16H 50/20* | (2018.01) | |
| *G06V 10/25* | (2022.01) | |
| *G06V 10/62* | (2022.01) | |
| *A61B 6/08* | (2006.01) | |

(52) U.S. Cl.
CPC .............. *A61B 6/0407* (2013.01); *A61B 6/06* (2013.01); *A61B 6/08* (2013.01); *A61B 6/405* (2013.01); *A61B 6/4007* (2013.01); *A61B 6/4014* (2013.01); *A61B 6/4021* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

SYSTEM AND METHOD OF IMAGE IMPROVEMENT FOR MULTIPLE PULSED X-RAY SOURCE-IN-MOTION TOMOSYNTHESIS APPARATUS USING ELECTROCARDIOGRAM SYNCHRONIZATION

The present invention claims priority to Provisional Application Ser. Nos. 63/182,426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

The present invention relates to a system and method of multiple pulsed X-ray source in-motion tomosynthesis imaging apparatus for acquiring images of lung influenced by a periodically moving heart.

BACKGROUND

Digital tomosynthesis systems typically use an X-ray source mounted at one end of a rotatable arm assembly and a digital X-ray flat panel detector at the other. Tomosynthesis can be used to screen for early signs of breast cancer in women and lung cancer in ordinary people with no symptoms. When tomosynthesis is performed, an X-ray source would need to move in an arc around the breast or lung. While the X-ray source is moving around the breast or lung, a series of low-dose X-ray images are acquired at different angles. Collected data set permits reconstruction of parallel planes. Each plane is in focus, and those that are out-of-plane tissue images are blurred. Usually, a wider sweep angle would generate more data projections and result in better 3D resolution, but it takes longer. Data processing is manufacturer-specific because different reconstruction algorithms might be used. However, heart beast will significantly influence the quality of X-ray imaging data for lung imaging because of periodically moving heart. Therefore, when the object moves, if X-ray image exposures are underway, blurring images is inevitable. However, conventional system haves only a single X-ray source at a cardiac rest with limited coverage and slow speed. The single X-ray source can only be at a specific location at a cardiac rest with a specific angle. Further, there are maybe missing data at a specific angle if such single source system speeds up data acquisition and reconstructions may suffer from motion artifacts and/or limited view angle artifacts. There are prior arts in cardiac-related imaging in computed tomography (CT) using ECG synchronization of gating, such as that in US20040077941A1.

SUMMARY

In a first aspect, a method to perform multiple pulsed source-in-motion tomosynthesis imaging includes capturing an electrocardiogram (ECG) waveform using an ECG sensor; evaluating the ECG waveform to validate a signal from the ECG sensor; using the ECG waveform as a basis for triggering multiple X-ray tomosynthesis sources; and scanning an object using the multiple pulsed sources of a tomosynthesis imaging device triggered by the ECG waveform.

In a second aspect, an imaging system includes an ECG sensor to generate an ECG waveform from an object; a tomosynthesis imaging device with multiple pulsed X-ray sources; and a processor coupled to the ECG sensor and the imaging device to perform tomosynthesis imaging by: capturing an ECG waveform using an ECG sensor; evaluating the ECG waveform to validate a signal from the ECG sensor; using the ECG waveform as a basis for triggering one or more X-ray sources; and scanning an object using a multiple pulsed source-in-motion tomosynthesis imaging system triggered by the ECG waveform.

In a further aspect, a system and method for improved image acquisition of multiple pulsed X-ray source in-motion tomosynthesis imaging apparatus generate the ECG waveform data using an electrocardiogram device. Once a representative cardiac cycle is determined, the system will acquire images only at the rest period of a heartbeat. Real-time ECG waveform is used as ECG synchronization for image improvement. Multi-source imaging apparatus avoids ECG peak pulse for better lung imaging under the influence of cardiac periodical motion. As a result, smoother data acquisition, much higher data quality can be achieved. The multi-source tomosynthesis machine is already distributed to multiple X-ray sources that are spanned at a wide angle. At the rest period of one heartbeat, X-ray exposures are from X-ray sources from different angles. Depending on the strength of motor, usually as many as 60 projections actual image acquisition process can be finished as fast as within two seconds for multiple pulsed X-ray source in-motion tomosynthesis imaging apparatus. Adding restriction of the rest period of heartbeat would improve image quality but it also slightly slowdown image acquisition.

Advantages of the system may include one or more of the following. The first advantage is that exposure from multiple pulsed X-ray sources spans a large angle at cardiac rest. The second advantage is that the source-in-motion location is programmable, so there is no missing data. The third advantage is the multiple source-in-motion can run much faster. Other advantages may arise when the multiple pulsed X-ray source-in-motion tomosynthesis imaging apparatus can take fast images with improved resolution when synchronized with ECG signals. As a result, real-time imaging and 4D imaging are also possible at multiple pulsed X-ray source-in-motion tomosynthesis imaging apparatus. It has a much low dose than that in CT. When the heart rate is low, the intervals between the heartbeats are nearly constant, and each mechanical contraction of the heart is nearly the same (e.g., Sinus rhythm with heart rate less than 65 beats), cardiac images taken by any modality will be of high diagnostic quality. The system provides high resolution images (such as when the heart rate changes suddenly and intermittently due to arrhythmias) when synchronized with ECG signals to acquire tomosynthesis imaging data while the heart is at a certain position that is substantially spatially stationary. One embodiment uses prospective gating, where the ECG signal is used to trigger data acquisition by the detector array at points in time when the heart is fairly stationary (typically during diastole) so that the radiographs used to reconstruct the image correspond to instants in time when the heart is fairly stationary. The imaging window is typically centered between about 60% and about 80% of a representative cardiac cycle (phase) duration. Different window widths and phases, including multiple phases, can be selected based on the choice of scanning protocol.

The resulting system is ideal for X-ray lung or breast imaging. The lung has regions with rest and movement phases with the rest phases of different regions ensuing at different points in time. The method and tomosynthesis imaging apparatus are of the type wherein multiple X-ray sources move around lung. The system obtains multiple projections during limited sweeping angle of the X-ray sources around the object to be examined.

BRIEF DESCRIPTION

DETAILED DESCRIPTION

The present invention will be described in detail by example with reference to the attached drawings in the following paragraphs. Throughout this description, the preferred embodiment and examples shown should be considered exemplars rather than limitations on the present invention. As used herein, the "present invention" refers to any one of the embodiments of the invention described herein and any equivalents. Furthermore, reference to various feature(s) of the "present invention" throughout this document does not mean that all claimed embodiments or methods must include the referenced feature(s).

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

Figure 1:
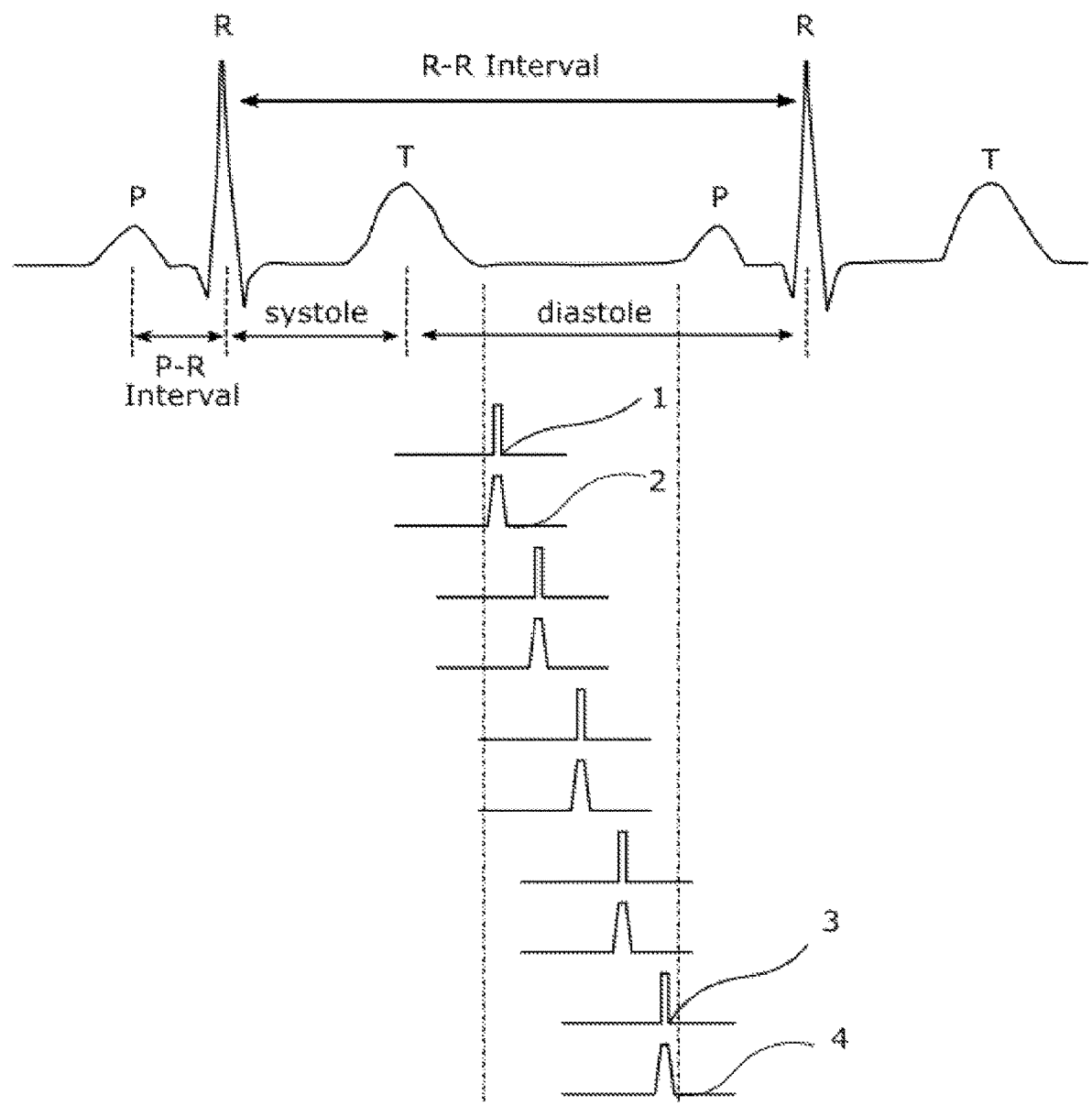
FIG. 1 illustrates timing diagram of X-ray exposure and motor speed for a multiple pulsed source-in-motion tomosynthesis imaging system in one cardiac period.

FIG. 1 shows X-ray imaging system timing diagram with a typical ECG diagram that illustrates one typical cardiac cycle for an ECG signal waveform, including a systolic phase—also known as systole, and a diastolic phase—also known as diastole, of the heart. The portions of the ECG signal labeled P, R and T are referred to as P wave, R wave and T wave, is typically the most prominent, highest amplitude, feature of the entire ECG signal. The cardiac cycle is typically defined as beginning with a P wave and continuing until the occurrence of a next P wave. An R-to-R interval—also known as 'RR interval'—is defined as beginning with an R wave and continuing until the occurrence of a next R wave. The graphical representation of an ECG signal includes a T wave, and a P wave. Analyzing the ECG signal with respect to the T wave, and the P wave allows more accurate phase information to be correlated with projection data as the heart rate changes. Multiple pulsed X-ray source-in-motion tomosynthesis imaging system can be programmed in such way that X-ray exposures only happen during cardiac rest.

X-ray sources 6 are spanned around a patient or an object, therefore generating multiple pulsed exposures. In the preferred embodiment the X-ray source 6 moves total about 4-5 inches from its original position after each exposure. In addition, x-ray source 6 can also be programmed to be at any location. In the preferred embodiment, to make sure all cardiac motion is accounted for and has been taken into account, all ECG heartbeats need to be considered as a sequence of data points.

One cardiac cycle or one heartbeat is an average time of about two seconds for each complete contraction of the heart. Thus, the total duration of the ECG can be within about two seconds or much shorter. There are groups of pulses, which would last about 0.1 to 0.2 seconds. For example, if the window to collect the cardiac cycle data at rest is 0.3 to 0.4 seconds long, the multiple pulsed X-ray source-in-motion tomosynthesis imaging system 5 could run its cycle several times. At the heart's maximum expansion, the X-ray images are taken during diastole. When the heart contracts there are no X-ray images are taken. The next set of X-ray images are taken at full expansion of the heart. That would be called gated tomosynthesis imaging. To accommodate motion between one heartbeat and another heartbeat, multiple pulsed X-ray source-in-motion tomosynthesis imaging system 5 is synchronized by the ECG waveform. This can result in the reconstruction of high-resolution images in real time.

Turning now to the ECG details, the R wave is the most important ECG signal for cardiac imaging. It is the electrical activity of the ventricles of the heart, namely the R wave, P wave and T wave. The amplitude of these waves corresponds to the amount of blood that the ventricles are pumping into the heart's arteries. It can also be detected by surface ECG. According to one embodiment of the present invention, X-ray source pulsing rate, pulse width, and intensity are controlled by synchronization with the R wave of the ECG signal of the patient's heartbeat. The benefit of ECG gating is that the heart will only be moving during one half of the cardiac cycle (i.e., during diastole). The potential of improving diagnosis performance of screening, detecting nodules earlier, and avoiding low-quality image data will provide an additional benefit to medical professionals.

The systole is an electrical contraction of the heart muscle to force blood out of the heart. Diastole is the relaxation phase of the heart, during which time the heart muscle is stretched to receive the oncoming flow of blood. The upper trace illustrates an electrocardiogram (ECG) waveform of a normal sinus rhythm at rest, taken from the top of the heart. An arrhythmia, or abnormal rhythm, of the heart, can cause these cardiac cycles to be irregular or cause portions of the cardiac cycle to occur outside of the atria so that only certain portions of the ECG are stationary at any given moment. These irregularities can create artifacts that blurs the resulting tomosynthesis image. Imaging at the systole phase is not ideal due to the movement of the heart.

Preferably, the diastole phase is used to capture channel ECG waveform data from the subject heart at rest. ECG waveform of the R wave, P wave and T wave can be captured and recorded into a computer in just several heartbeat cycles. After taking average or other algorithms, a single resting period can be determined. After selection of a resting period, gating parameters are set.

Figure 2:
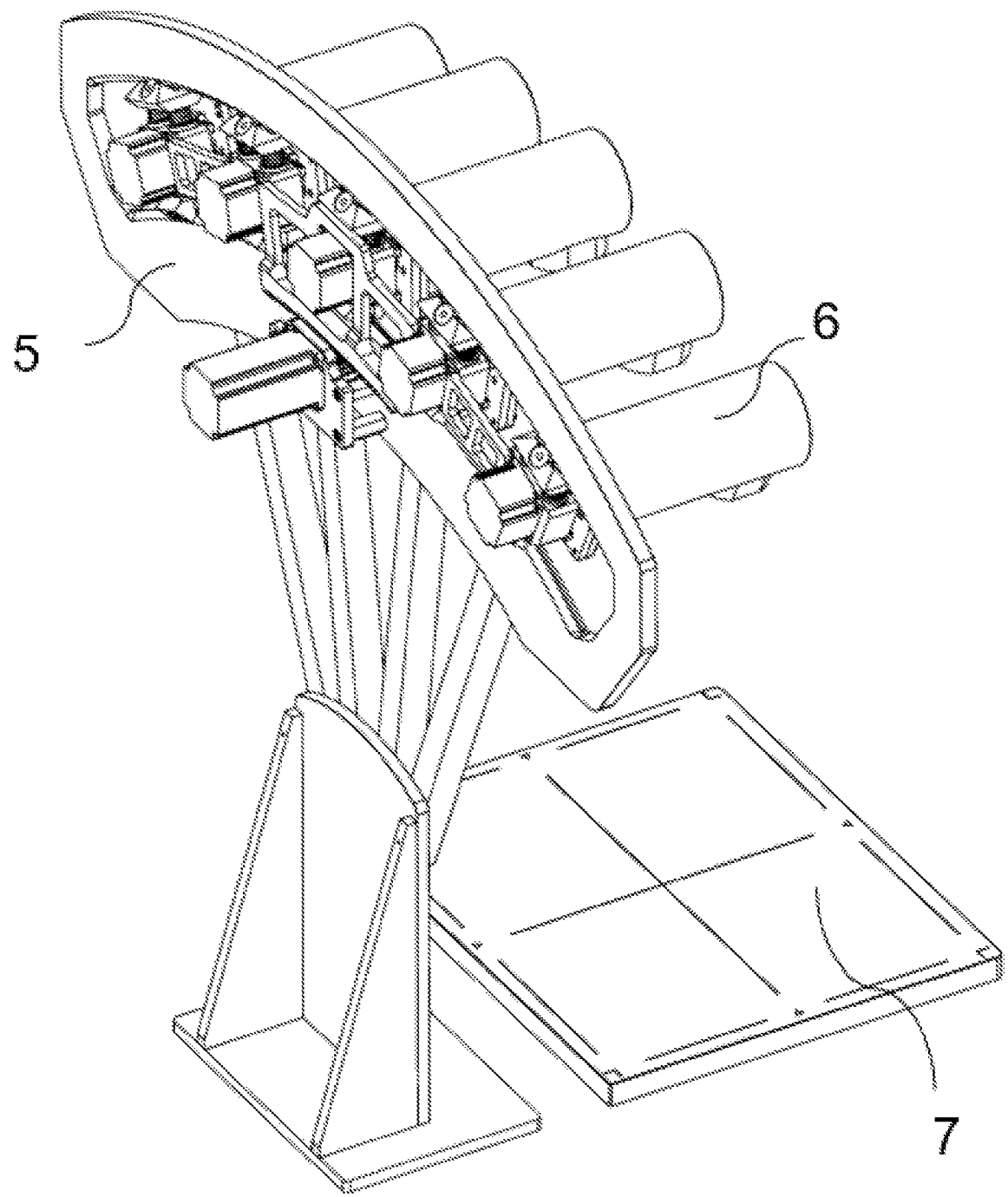
FIG. 2 shows a multiple pulsed X-ray source-in-motion tomosynthesis imaging system.

Referring to FIG. 2 about the multiple pulsed X-ray source tomosynthesis system 5, each X-ray source 6 is sitting on a separate motor stage. All X-ray source exposure timing and motor stage speed are programmable. In timing diagram, first X-ray source exposure 1 is triggered when first motor stage speed 2 reaches constant speed. Next motor stage will move and next X-ray source exposure will be triggered in the same way. In this example, there are five X-ray sources 6 and five motor stages. Last X-ray source exposure 3 is trigged when last motor stage speed 4 momentarily reach constant.

In the timing diagram, whole X-ray exposure from the first X-ray source exposure 1 to last X-ray source exposure 3 lasts about a fraction of second. For example, typical exposure time of this kind source is about 40 ms, so five X-ray sources will need at least about 200 ms or 0.2 s. It will generally fit into the rest period of the diastole phase. The length of the resting period may vary based on a number of factors including physical condition and physiology of the patient. Therefore, after selection of a resting period, additional gating parameters are set.

Figure 3:
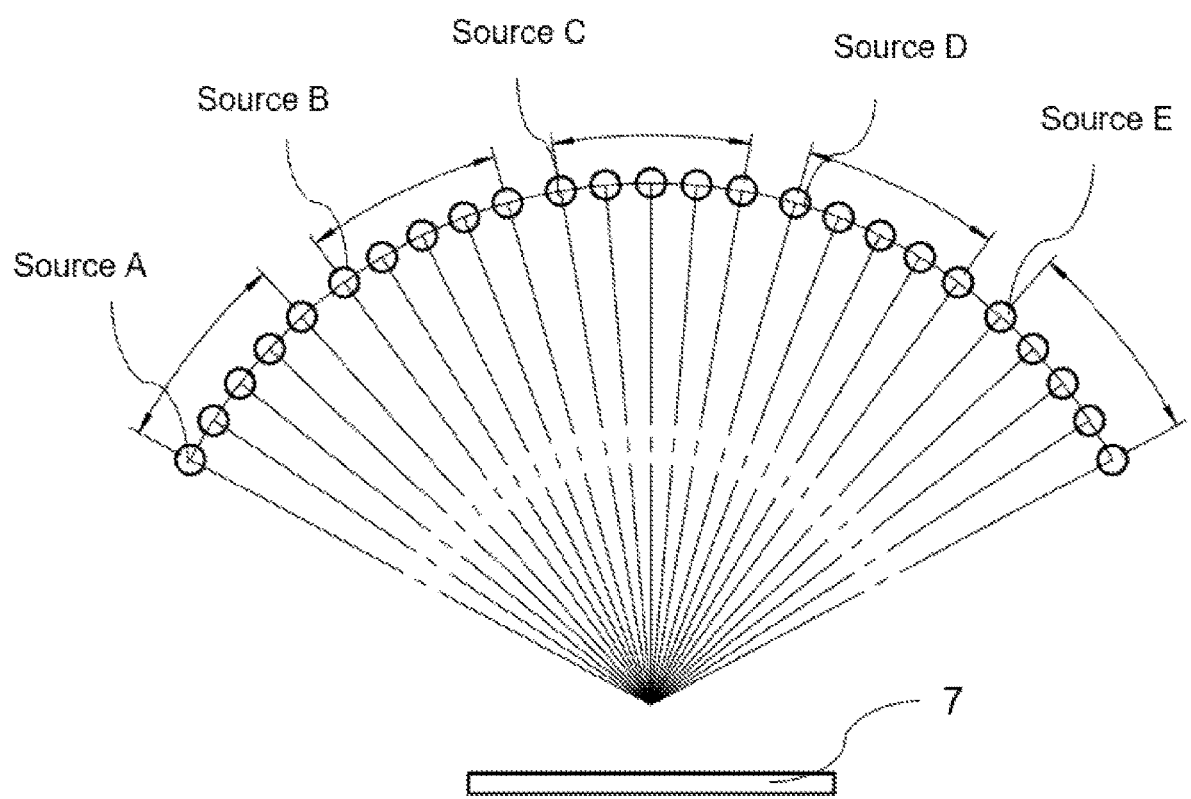
FIG. 3 shows angle spans with multiple pulsed X-ray source-in-motion tomosynthesis imaging system during cardiac period.

In one embodiment, each motor is of the tomosynthesis imaging system is operated to drive one of drive assemblies to rotate about the pivot point, while the other drive assembly is stationary. X-ray source 6 generates X-rays when the object is in position between source and X-ray flat panel detector 7. A representation of the movement of source is shown in FIG. 3 by arrow in which the source is at a location. The motor moves the x-ray source across the heart. A patient breathes naturally as the apparatus acquires an ECG-synchronized image. Typically, rotation and translation (and deformation) of rigid body and its components will cause image degradation and loss of spatial resolution and image contrast, but the data acquired during the time that the x-ray source is passing through various positions provides for reconstruction and viewing of multiple parallel planes that can be reconstructed to provide a three-dimensional image. Data from each plane can be used to construct a single view of the anatomy. In the alternative, the image processing software could analyze multiple slices from one or more planes and create a three-dimensional image from those partial views.

The P wave, R wave, and T wave represent electrical signals in heart. P wave indicates the beginning of atrial contraction, and it is followed by a negative deflection that represents the atrial repolarization. The interval between P waves and R wave is usually called PR interval. The normal PR interval measures 0.12-0.20 seconds. The interval between two successive R waves represents the duration of the contraction of the ventricle. For heart imaging under ECG synchronization gating, ECG lead is attached to a patient's body near chest wall or to the body using a chest belt ECG device so that ECG signal can be received by a medical device.

The T wave is shown in the electrocardiogram and represents a phase of the cardiac cycle, where the electrical activity of the heart muscle is opposite to that of its action potential. It is shown with an arrowed line for convenience. However, the T wave is not intended to represent the signal level of the electrocardiogram.

FIG. 2 shows a novel type of X-ray imaging system using multiple pulsed X-ray sources-in-motion to perform high-efficient and ultrafast 3D radiography. There are multiple pulsed X-ray sources 6 mounted on a structure in motion to form an array of sources. The multiple X-ray sources 6 move simultaneously relative to an object on a predefined arc track at a constant speed as a group. Each individual X-ray source 6 can also move rapidly around its static position in a small distance. When an X-ray source 6 has a speed that is equal to group speed but with opposite moving direction, the X-ray source 6 and X-ray flat panel detector 7 are activated through an external exposure control unit so that source stay momentarily standstill. It results in much reduced source travel distance for each X-ray source 6. 3D scan can cover much wider sweep angle in much shorter time and image analysis can also be done in real-time. This type of X-ray imaging system utilizes much more X-ray sources 6 than other types of X-ray imaging system in order to achieve much higher scan speed. Because of multiple sources are used, it is necessary to ensure that every X-ray source 6 is functioning so that whole machine is running.

Referring to timing diagram of FIG. 1, in one embodiment, X-ray source exposure 1 is triggered when vibration motor has opposite direction as that of sweeping motor but has the same speed as that of sweeping motor. However, during cardiac period, region of lung position is influenced by heartbeats, therefore image blurring is inevitable if exposure does not occur at a reset period of a heartbeat. The multiple pulsed X-ray source tomosynthesis imaging system 5 with ECG synchronization performs like following: first, capturing an ECG waveform using an ECG sensor; second, evaluating the ECG waveform to validate a signal from the ECG sensor; third, using the ECG waveform as a basis for triggering X-ray source exposure and motion speed control; last, scanning an object and acquiring X-ray images based on trigger provided by the ECG waveform.

In one embodiment, the vibration motor provides low vibration energy to adjust movement of multiple pulsed X-ray source at cardiac rest. Real time ECG waveform is used as ECG synchronization for image improvement. Real time data acquisition of multiple pulsed X-ray source-in-motion tomosynthesis imaging system 5 would acquire images only at rest period of heart beat. Real time ECG waveform is used as ECG synchronization for image improvement. Real time ECG waveform is used as ECG synchronization for image improvement.

Sweeping motor rotates arm in an arc to allow source to sequentially position between angles, to provide X-ray exposure during time interval. Exposure to target can be scanned at regular rate, variable rate or pulsed exposure depending on the requirement of patient. This is part of preferred embodiment for 4D imaging with multiple pulsed X-ray sources that it would also synchronize real time cardiac cycle ECG signal to image acquisition process. ECG signal will drive an actuator such as solenoid or sweeping motor to move arm at speed of heart beat while the rest is stationary. Arm and X-ray source move together while making pulsed exposure on a series of positions during time interval and acquire imaging data within a given time intervals. Due to ECG synchronization during this entire motion, all images are acquired while the heart is moving smoothly. If cardiac motion ceases, then imaging will cease. Real time ECG signal of the patient is used to synchronize image acquisition by moving arm and X-ray source 6 simultaneously with heart beat of the patient. Real time ECG signal of the patient is used to synchronize image acquisition by moving arm and X-ray source simultaneously with heart beat of the patient.

X-ray sources 6 generate X-ray beam which pass through the breast, lung or body tissues of the patient. X-ray flat panel detector 7 acquire data set which comprises number of real time data acquired at different angles. For each sourcein-motion X-ray source, ECG waveform is available. Using an ECG waveform synchronizer ECG synchronization for image improvement can be implemented using actual ECG signal to get correct timing point of each data acquisition process. ECG waveform synchronizer sends signals to each data acquisition controller to control the X-ray source movement for precise timing of data acquisition. ECG waveform generator produces heart beat trigger signal that triggers the entire data acquisition system to start data acquisition at rest period of the cardiac cycle and stops data acquisition at cardiac periodical motion. This results in elimination of blurring images caused by cardiac periodical motion artifact. Each ECG waveform data synchronization allows seamless data acquisition to run much faster than that in prior art. As a result, total scanning speed is much faster than that in prior art. This will give better quality images with smooth data.

A supporting frame structure holds an array of multiple X-ray sources 6. The array is mounted on the supporting frame structure such that each X-ray source is disposed at one end of a rotatable arm assembly and such that each X-ray source can be independently rotated to a different angular position. Each arm assembly supports a respective X-ray flat panel detector. Multiple arm assemblies may be provided with a single supporting frame structure. In this arrangement, a respective arm assembly, a respective X-ray flat panel detector, and a respective X-ray source may be positioned adjacent each other so as to permit radiation from a corresponding X-ray source to pass through a portion of the subject during the acquisition of a given tomosynthesis data set. In certain embodiments, more than one X-ray source may be activated simultaneously. In one example, up to four or six X-ray sources may be activated simultaneously. In another example, eight X-ray sources may be activated simultaneously. In another example, sixteen X-ray sources may be activated simultaneously. A processing unit with FPGA logic, processor or computer controls the activation of individual X-ray sources and coordinates the operation of all X-ray sources in a time-division multiplexed manner.

FIG. 3 shows total scan sequence from different source on different motors at different angle and different time. Source A, Source B, Source C, Source D, Source E are sources on different motors, X-ray exposures from A, B, C, D, E will occur within one cardiac period that defined at FIG. 1. Those exposures from different angles. After the first five exposures, each of the plurality of motors will move to next position and do another five exposures in another cardiac period. in this case, there are five motors. Therefore, total 25 exposures can be achieved within five heartbeat period in this example. Depending each source exposure time needed, it is possible to achieve 25 exposures below five heartbeats.

X-ray sources 6 can be independently powered and controlled for multiple exposures. Because they are located on the rotatable X-ray arm assembly, each source can be pointed to a different location and at a different angle for sequential exposure of objects to create a corresponding number of data sets. Different data sets can be processed to generate images at specific image view angles and 3-dimensional (3D) image volume. Based on the above characteristics, images acquired by each pulsed X-ray source can be combined into corresponding 3D data set for combined data set with high-quality images to improve the accuracy of final diagnostic imaging results. It should be noted that combined data set may also contain spatially related information of two or more different projection data sets to achieve true 3-dimensional representation of desired data set. When projection data sets are superimposed, spatially related information of each data set is retained in composite 3D data set for diagnostic purposes.

X-ray flat panel detector 7 has the capability to acquire images when multiple pulsed X-ray sources are scanning in-motion or at rest period of one heartbeat. At cardiac rest, one X-ray source 6 is in rotation around the object for an arc trajectory with a constant distance to object. During heartbeats, when another pulsed X-ray source is static. The sequence repeats itself until all static pulses are delivered for each heartbeat. Since X-ray pulses come from different angles, a real-time image acquisition process can be completed within at about two seconds. At this moment, different data acquisition patterns can also be used. It would be useful to use other patterns to acquire other tomosynthesis images. Those skilled in the art could determine which patterns should be applied based on the purpose of imaging.

The ECG pulse should be first detected and synchronized with the multiple pulsed X-ray source. The operator needs to set a proper position and time point for a heartbeat cycle in a computer program that has real-time ECG waveform. It will tell the system to acquire images at specific locations in a time sequence based on data from the ECG sensor when the heart is almost in a rest position. In other words, when heart rate is relatively low, if X-ray images are acquired when the heart is at rest, it will have good quality. If there is no synchronization, data acquisition from multiple sources will have different positions in relation to a stationary breast or lung. It means they can't be reconstructed into a single view. A representative cardiac cycle means a full range of a heart's periodic motion; a signal of a representative cardiac cycle means a whole period of a periodic motion of a heart. According to my invention, a multiple pulsed X-ray source tomosynthesis system 5 is provided for obtaining images of moving subjects, including the heart, by using multiple pulsed X-ray sources arranged in a pattern around an axis extending from a center of a body of a patient to a periphery of the body of the patient.

The ECG data is acquired using an ECG sensor. A representative cardiac cycle is determined by averaging many cardiac cycles of actual patients. Image is obtained only during the rest period of the representative cardiac cycle. The ECG signal is captured by analog or digital electrodes on patient's body surface. An ECG lead will have three electrodes. Two are located near the heart to detect the heart's electrical signal. ECG data can be further processed by an analog-to-digital converter and then passed to the image processing system. First, we need to process ECG waveform in order to get a synchronization signal for image acquisition. There are many ECG waveform processing methods described in medical imaging that may be used to achieve this. Once the representative cardiac cycle is determined, it is possible to predict future locations of the next representative cardiac cycle and make appropriate exposure adjustments in advance. By capturing images during diastole, we can improve image quality and decrease radiation dose at tomosynthesis imaging. Because we need to capture data during a specific phase and control the moving X-ray source and camera to be spatially stationary within a certain angle and duration, multiple pulsed X-ray source-in-motion tomosynthesis 5 imaging apparatus can be utilized to generate high-quality tomosynthesis imaging data.

The multiple pulsed source-in-motion tomosynthesis imaging system 5 can use ECG signals/waveforms for synchronizing with the motion of the object of imaging to capture images at a specific moment of the cardiac cycle by which motion artifacts are eliminated or reduced. The specific moment of the cardiac cycle depends on cardiac rate, and it can be determined based on initial or previous average R-R interval. The patient, or objects' motion artifacts can then be corrected using computer reconstruction algorithms after capturing at specific moments of the cardiac cycle. Average R-R interval, the ratio of one heartbeat to another, may be done within one minute. Therefore, during a high heart rate period additional tomosynthesis image acquisitions with smaller window widths or windows can be performed during the same time period. Average R-R interval will depend on the speed of motion. If cardiac motion is slower, then the average R-R interval would be longer.

In one embodiment, the ECG synchronization for image acquisition uses the heartbeat time interval between two beats (the cardiac period). When cardiac images are taken with the same cardiac period, each X-ray image exposure is made at the same phase of the cardiac cycle. As a result, each projection data set acquired during a different cardiac cycle phase can be used to generate a high-quality final reconstructed image. The techniques rely on synchronization of gating to acquire whole projection data sets during different phases of the cardiac cycle using a gating window (diastole). The rate of acquiring the projection data set becomes limited by the periodicity of the cardiac cycle. A source-in-motion system should not acquire projection data sets that overlap or might cause other overlaps.

The ECG waveform of heartbeat is used to determine cardiac periodical motion in ECG synchronization. With ECG synchronization, image quality improvement can be achieved in several ways. First way is to acquire data only when the object is resting with less chance of blurring due to periodic motion. It would reduce unnecessary multiple imaging exposures, which in turn reduce radiation dose. Second, by having better-synchronized data, there is more chance to reconstruct high resolution three-dimensional (three-dimensional) volume images. The higher the data quality, the easier the reconstruction. Furthermore, reduced radiation dose means reduced breast tissue necrosis and reduced lung tissue lesions, which are primary causes of false-positive diagnoses in radiologists' report.

The current system detects an R wave in the ECG waveform that may be used as a basis for image data acquisition. ECG synchronization for image improvement works with the multi-source imaging apparatus and avoids ECG peak pulse for better lung imaging under the influence of cardiac periodical motion. As a result, high data quality can be achieved using the multiple pulsed source tomosynthesis system with distributed multiple X-ray sources that are spanned at wide angle. At the rest period of one heartbeat, X-ray exposures are from X-ray sources from different angles.

In an embodiment of the invention, a multiple pulsed source tomosynthesis imaging system can be an X-ray source-in-motion assembly with multiple X-ray sources arranged in a pattern to span a wide view angle when in motion, an X-ray detector array, and an ECG synchronization unit coupled to the X-ray source-in-motion assembly. The ECG synchronization unit is used to control the timing of X-ray exposures so that there is no X-ray exposure at heart peak beating. As a result, the image data set acquired during cardiac rest will be of high quality. When the object is moving, if X-ray image exposures are underway, blurring images are inevitable. The X-ray source-in-motion tomosynthesis imaging apparatus can use ECG synchronization at X-ray pulse peak of heartbeat. In one embodiment, a heart rate of about 65 beats per minute (bpm) can be tracked by ECG and the frame rate would increase when the heart rate is low because the imaging window can be bigger. Multiple pulsed X-ray source-in-motion tomosynthesis imaging apparatus uses real-time ECG synchronization.

Additionally, used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features. Also as used herein, the phrase "reconstructing an image" is not intended to exclude embodiments of the present invention in which data representing an image is generated but a viewable image is not. However, many embodiments generate (or are configured to generate) a viewable image.

Various modifications and alterations of the invention will become apparent to those skilled in the art without departing from the spirit and scope of the invention, which is defined by the accompanying claims. It should be noted that steps recited in any method claims below do not necessarily need to be performed in the order they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Although the invention is described above in terms of various exemplary embodiments and implementations, it should be understood that the various features, aspects, and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open-ended as opposed to limiting. As examples of the foregoing: the term "including" should be read as meaning "including, without limitation" or the such as; the term "example" is used to provide exemplary instances of the item in the discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A method to perform multiple pulsed X-ray source-in-motion tomosynthesis imaging, comprising:
    capturing an electrocardiogram (ECG) waveform using an ECG sensor;
    evaluating the ECG waveform to validate a signal from the ECG sensor;
    using the ECG waveform as a basis for moving each of motor stages and triggering multiple pulsed X-ray tomosynthesis sources; and
    acquiring images by scanning an object and using the multiple pulsed sources-in-motion tomosynthesis imaging apparatus triggered by the ECG waveform.

2. The method of claim 1, comprising using a sequence of data points to produce a virtual 3-dimensional (3D) model.

3. The method of claim 1, comprising generating at each heartbeat, a 3D surface with a predetermined point density towards the center of the heart.

4. The method of claim 1, comprising determining a number of 3D models needed for a predetermined image quality specified by a clinical protocol.

5. The method of claim 1, comprising removing noise and acquiring real time live data meeting one or more ECG criteria during diastole.

6. The method of claim 1, comprising capturing gated tomosynthesis images from the imaging system.

7. The method of claim 1, comprising capturing X-ray exposures from multiple X-ray sources at different angles at a rest period of a heartbeat.

8. The method of claim 1, comprising capturing at least 60 projection images within two seconds.

9. The method of claim 1, comprising sequencing motor actuations and X-ray exposures within a diastolic cycle.

10. The method of claim 1, comprising:
    using multiple pulsed X-ray sources in motion by positioning a primary motor stage and one or more secondary motor stages to a predetermined initial location;
    sweeping the primary motor stage at a predetermined constant speed by said primary motor;
    oscillating each of the secondary motor stages by a corresponding secondary motor with a predetermined sequence based on the ECG waveform;
    electrically activating an X-ray source and an X-ray flat panel detector when a secondary motor stage moves in an opposite direction to that of the primary motor stage and at a selected speed of the primary motor stage; and
    acquiring image data from the X-ray source with the X-ray flat panel detector.

11. A multiple pulsed X-ray source-in-motion tomosynthesis imaging system, comprising:
    an electrocardiogram (ECG) sensor to generate an ECG waveform from an object; and
    a multiple pulsed X-ray source-in-motion tomosynthesis imaging apparatus; and
    a processor coupled to the ECG sensor and the imaging apparatus to perform X-ray tomosynthesis imaging by:
    capturing an electrocardiogram (ECG) waveform using an ECG sensor;
    evaluating the ECG waveform to validate a signal from the ECG sensor;
    using the ECG waveform as a basis for moving each of motor stages and triggering multiple pulsed X-ray tomosynthesis sources; and
    acquiring images by scanning an object and using the multiple pulsed sources-in-motion tomosynthesis imaging apparatus triggered by the ECG waveform.

12. The system of claim 11, comprising one or more X-ray sources that standstill during an X-ray pulse trigger exposure duration based on the ECG waveform.

13. The system of claim 11, comprising an X-ray flat panel detector to acquire 3D radiography image projection data with a predetermined sweep over a predetermined time based on the ECG waveform, and wherein image analysis is done in real-time during scanning.

14. The system of claim 11, comprising one or more X-ray source tubes randomly activated from one of any sources in the array using a random-firing scheme based on the ECG waveform.

15. The system of claim 11, wherein 3D X-ray radiography images are reconstructed based on each image with an angled geometry of X-ray source tube.

16. The system of claim 11, comprising:
    an X-ray exposure control unit;
    a predefined track; and
    a source array including the multiple pulsed X-ray source tubes mounted on a structure in motion, wherein each of the multiple pulsed X-ray source tubes moves simultaneously around an object on the pre-defined track at a constant speed of a group, and when an individual X-ray source tube has a speed that equals to group tube speed but in an opposite moving direction, the individual X-ray source tube is triggered through the exposure control unit; and
    an X-ray flat panel detector to receive X-ray flux and to generate imaging data.

17. The system of claim 11, comprising using a sequence of data points to produce a virtual 3-dimensional (3D) model.

18. The system of claim 11, comprising generating at each heartbeat, a 3D surface with a predetermined point density towards the center of the heart.

19. The system of claim 11, comprising determining the number of 3D models needed for a predetermined image quality in accordance with a clinical protocol.

20. The system of claim 11, comprising removing noise and acquiring real time live data meeting one or more ECG criteria during diastole.

* * * * *